United States Patent [19]

Ozmen et al.

[11] Patent Number: 5,399,787
[45] Date of Patent: Mar. 21, 1995

[54] OLEFIN ISOMERIZATION PROCESS USING ETHERIFICATION FEED ISOMERIZATION

[75] Inventors: Suleyman M. Ozmen, Winnetka; Paul J. Kuchar, Hinsdale, both of Ill.

[73] Assignee: UOP, Des Plaines, Ill.

[21] Appl. No.: 123,671

[22] Filed: Sep. 20, 1993

[51] Int. Cl.$^6$ .............................................. C07C 41/06
[52] U.S. Cl. ...................................... 568/697; 585/315
[58] Field of Search .......................... 568/697; 585/315

[56] References Cited

U.S. PATENT DOCUMENTS 4,554,386  11/1985  Groeneveld et al. ................ 568/697

*Primary Examiner*—Howard T. Mars

*Attorney, Agent, or Firm*—Thomas K. McBride; John F. Spears, Jr.; Reginald K. Taylor

[57] ABSTRACT

In a process for producing tertiary alkyd ethers from an olefinic hydrocarbon feedstock, undesirable normal alkanes are removed from the process by passing at least a portion of a hydrocarbon process stream to an alkane isomerization zone to convert normal alkane to isoalkane and passing the alkane isomerization zone effluent to a separation zone to remove the isoalkane. Since no normal alkane is discharged from the process, the loss of valuable olefins, which have boiling points close to normal alkane, is prevented and olefins are retained in the process and converted to the appropriate tertiary alkyl ether. The result is an increase in the ether yield.

22 Claims, 4 Drawing Sheets

OLEFIN ISOMERIZATION PROCESS USING ETHERIFICATION FEED ISOMERIZATION

FIELD OF THE INVENTION

The invention relates to a process for the production of ether by the reaction of an alcohol with an isoolefin. More specifically, this invention relates to a process for the production of ether and the skeletal isomerization of olefins to provide additional feedstock for the production of ethers.

BACKGROUND OF THE INVENTION

Olefinic hydrocarbons are feedstocks for a variety of commercially important reactions to yield fuels, polymers, oxygenates and other chemical products. The specific olefin isomer, considering the position of the double bond or the degree of branching of the hydrocarbon, may be important to the efficiency of the chemical reaction or the properties of the product. The distribution of isomers in a mixture of olefinic hydrocarbons is rarely optimum for a specific application. It is often desirable to isomerize olefins to increase the output of the desired isomer.

Butenes are among the most useful of the olefinic hydrocarbons having more than one isomer. A high-octane gasoline component is produced from a mixture of butenes in many petroleum refineries, principally by alkylation with isobutene; 2-butenes (cis- and trans) generally are the most desirable isomers for this application. Secondary butyl alcohol and methylethyl ketone, as well as butadiene, are other important derivatives of 2-butenes. Demand for 1-butene has been growing rapidly, based on its use as a co-monomer for linear low density polyethylene and as a monomer in polybutene production. Isobutene finds application in such products as methyl methacrylate, polyisobutene and butyl rubber. The most important derivative influencing isobutene demand and butene isomer requirements, however, is methyl tertiary butyl ether (MTBE) which is experiencing rapid growth in demand as a gasoline component.

Pentenes are also valuable olefinic feedstocks for fuel and chemical products. Isoprene, which may be produced by the dehydrogenation of isopentene or by the extraction of steam cracker $C_5$ hydrocarbon product, is an important monomer in the production of elastomers. To an increasing extent, pentenes obtained from refinery cracking units are alkylated with isobutane to obtain a high octane gasoline component. The principal influence on trends in isopentene demand and pentene isomer requirements, however, is the rapid growth and demand for tertiary amyl methyl ether (TAME) as a gasoline component. TAME is of increasing interest as restrictions on gasoline olefins and volatility reduce the utility of pentenes as a gasoline component. This interest may extend to hexenes and higher olefins having tertiary carbons which could be reacted to yield high octane ethers.

Only rarely are olefin isomers obtained in a refinery or petrochemical product in a ratio-matching product demand. In particular, there is a widespread need to increase the proportion of isobutene, isopentene and other tertiary-carbon olefins for the production of MTBE, TAME, ethyl tertiary butyl ether (ETBE), and tertiary amyl ethyl ether (TAEE).

Processes for the production of such ethers have suffered from a shortage of the isoolefins necessary for reaction with the alcohols to provide the desired ethers. Feed streams for etherification processes typically consist of a wide variety of olefinic and paraffinic isomers. The availability Of etherification feedstocks have been increased through the dehydrogenation of paraffins and through the skeletal isomerization of olefins.

The skeletal isomerization of olefins involves the reorientation of the molecular structure in respect to the formation or elimination of side chains. More particularly, skeletal isomerization relates to the conversion of unbranched olefins into branched olefins having the same number of carbon atoms. The skeletal isomerization of olefins is known to be accomplished by contacting unbranched or slightly branched olefins with an acidic catalyst at elevated temperatures. The process is generally applicable to olefins having about 4 to about 20 carbon atoms per molecule and is especially applicable to olefins having about 4 to about 10 carbon atoms per molecule. The process may be used to form isobutene from normal butenes.

U.S. Pat. No. 4,554,386 (issued to Groeneveld) discloses a combination etherification and skeletal isomerization process for making MTBE. In this process, a first MTBE reactor is supplied with an isobutene-containing hydrocarbon stream and a methanol stream. These streams are then reacted in the presence of an etherification catalyst. The effluent from the MTBE reactor is sent to a first MTBE separation column. From this column, MTBE is discharged from the bottom and a stream containing unconverted isobutene, methanol, side products (e.g. dimethyl ether), normal butenes, and butanes are discharged as overhead and recycled to the isomerization reactor. The effluent from the isomerization reactor is sent to a second MTBE reactor to complete the etherification/alkene isomerization loop. To avoid the buildup of alkanes in the system, lower molecular weight hydrocarbons are purged using a fractionation column.

The problem with discharging or purging light ends from an olefin isomerization process by fractionation is that the light ends contain a significant amount of valuable alkenes which can be lost along with the undesirable alkanes because the boiling points of the alkenes are very close to the boiling points of the alkanes, i.e., the boiling points of the isoalkenes used for ether production are between the boiling points of the alkanes that are to be purged. As a result of the loss of these alkenes, the overall ether yield is reduced.

There is a need for an alkane isomerization process that avoids the buildup of alkanes in the process without the loss of valuable alkenes.

SUMMARY OF THE INVENTION

In a process for producing tertiary alkyl ethers from olefins, undesirable normal alkanes are removed by processing at least one of the hydrocarbon process streams in an etherification/alkene isomerization loop to an alkane isomerization zone to convert normal alkanes to isoalkanes and then removing the isoalkanes in a separation zone. The objective of removing normal alkanes from the etherification/alkene isomerization loop can be accomplished in many ways by varying the position of the alkane isomerization zone along the loop. For example, in one embodiment of the present invention, the alkane isomerization zone is positioned upstream of the etherification zone. In another embodiment of the present invention, the alkane isomerization zone is located downstream of the etherification zone. Since isoalkanes have boiling points that are less than the alkenes used to produce the tertiary ether, the isoalkane can be separated from the etherification feed without losing the desirable alkenes. As a result, the overall olefin utilization increases, thereby increasing ether yields.

The present invention is a process for removing normal alkanes from an etherification/isomerization method which reacts an olefinic hydrocarbon stream with an alcohol in an etherification zone to produce an etherification zone effluent stream, separates the etherification zone effluent stream in a first separation zone to produce an ether product stream and a first separation zone effluent stream, passes the first separation zone effluent stream to a skeletal isomerization zone to form an isoalkene-containing isomerate, and recycles the isoalkene-containing isomerate to the etherification zone, the removal process comprising the steps of passing at least a portion of at least one of the streams to an alkane isomerization zone to convert the normal alkane to isoalkane and removing the isoalkane in a second separation zone.

In one embodiment, the present invention is a process for the production of a tertiary alkyl ether from an olefinic hydrocarbon feedstock comprising normal alkane and isoalkane which process comprises the steps of: contacting at least portion of the feedstock with an isomerization catalyst in an alkane isomerization zone under conditions to selectively convert the normal alkane to isoalkane to produce an alkane isomerization zone effluent stream; passing at least a portion of the alkane isomerization zone effluent stream to a first separation zone to produce a first separation zone effluent stream and to remove isoalkane; contacting at least a portion of the first separation zone effluent stream with an etherification catalyst in an etherification zone at etherification conditions to react the isoalkene with a $C_1$–$C_5$ monohydroxy alcohol to produce an etherification zone effluent stream comprising the ether and normal alkane; passing at least a portion of the etherification zone effluent stream to a second separation zone to produce an ether product stream and a second separation zone effluent stream comprising normal alkene; contacting at least a portion of the second separation zone effluent stream with an isomerization catalyst in an alkene isomerization zone at isomerization conditions to convert the normal alkene to isobutene, thereby producing an isoalkene-containing isomerate; and recycling at least a portion of the isoalkene-containing isomerate to the alkane isomerization zone.

In another embodiment, the present invention is a process for the production of methyl tertiary butyl ether from an olefinic hydrocarbon feedstock comprising normal butane and isobutane which process comprises the steps of: contacting at least a portion of the feedstock with an isomerization catalyst in a butane isomerization zone under conditions to selectively convert the normal butane to isobutane to produce a butane isomerization zone effluent stream; passing at least a portion of the butane isomerization zone effluent stream to a first separation zone to produce a first separation zone effluent stream and to remove isobutane; contacting at least a portion of the first separation zone effluent stream with an etherification catalyst comprising a macroporous acid-form sulfonated solid resin in an etherification zone at etherification conditions to react the isobutene with a methanol to produce an etherification zone effluent stream comprising the methyl tertiary butyl ether and the normal butene; passing at least a portion of the etherification zone effluent stream to a second separation zone to produce a methyl tertiary butyl ether product stream and second separation zone effluent stream comprising normal butene; contacting at least a portion of the second separation zone effluent stream with an isomerization catalyst in a butene isomerization zone at isomerization conditions to convert the normal butene to isobutene, thereby producing an isobutene-containing isomerate; and recycling at least a portion of the isobutene-containing isomerate to the butane isomerization zone.

In another embodiment, the present invention is a process for the production of methyl tertiary butyl ether from an olefinic hydrocarbon feedstock comprising normal butane and isobutane which process comprises the steps of: passing the olefinic feedstock into a selective hydrogenation zone; contacting at least a portion of the resulting feedstock with an isomerization catalyst in a butane isomerization zone under conditions to selectively convert the normal butane to isobutane to produce a butane isomerization zone effluent stream; passing at least a portion of the butane isomerization zone effluent stream to a first reactive-distillation zone to produce a first reactive-distillation zone effluent stream and to remove isobutane; contacting at least a portion of the first separation zone effluent stream with an etherification catalyst comprising a macroporous acid-form sulfonated solid resin in an etherification zone at etherification conditions to react the isobutene with a methanol to produce an etherification zone effluent stream comprising the methyl tertiary butyl ether and the normal butene; passing at least a portion of the etherification zone effluent stream to a second reactive-distillation zone to produce a methyl tertiary butyl ether product stream and a second reactive-distillation zone effluent stream comprising normal butene; passing the second reactive distillation zone effluent stream to a water wash tower wherein the second reactive distillation zone effluent stream is contacted with water to produce a raffinate stream comprising normal butene and an extract stream comprising water and methanol; contacting at least a portion of the raffinate stream with an isomerization catalyst in a butene isomerization zone at isomerization conditions to convert the normal butene to isobutene, thereby producing an isobutene-containing isomerate; and recycling at least a portion of the isobutene-containing isomerate to the butane isomerization zone.

DESCRIPTION OF THE PREFERRED EMBODIMENT

Figure 1:
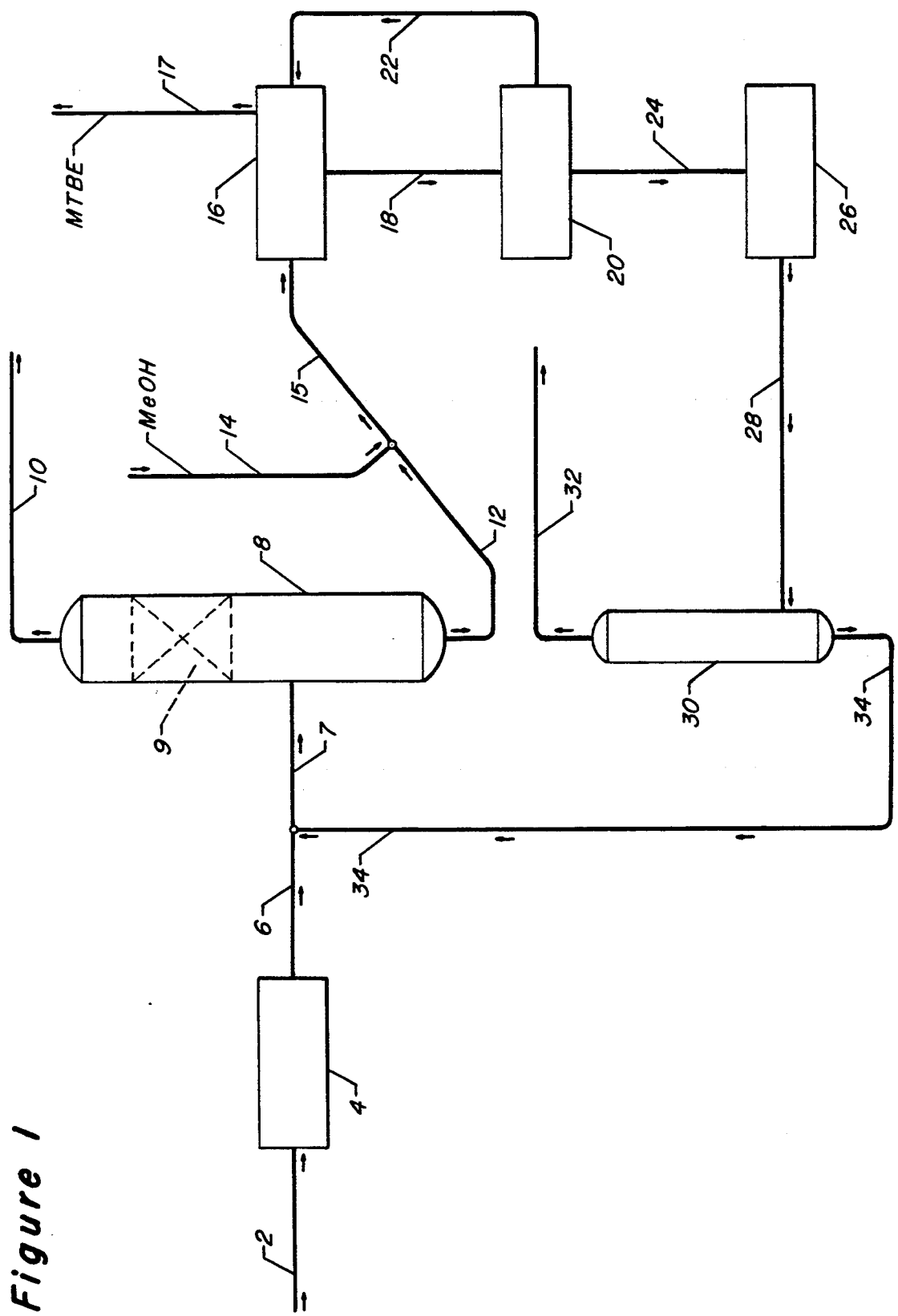
FIG. 1 is a schematic drawing of one embodiment of the present invention.

This invention is broadly applicable to the production of a wide variety of ethers from a number of different olefinic hydrocarbon feedstocks. The primary ethers for which this invention will be applied are tertiary amyl and tertiary butyl ethers. Where the etherification process is one for the production of butyl ethers, the typical olefinic hydrocarbon feedstock will consist of a mixture of $C_4$ isomers comprising isobutane, isobutene, normal butane, 1-butene, trans-2-butene and cis-2-butene. Where the process is one for the production of amyl ethers, the olefinic hydrocarbon feedstock will include 3-methyl-1-butene, isopentane, 1-pentene, 2-methyl-1-butene, normal pentane, trans-2-pentene, cis-2-pentene and 2-methyl-2-butene in a typical distribution of isomers. Although a variety of sources are available to provide such olefinic hydrocarbon feedstocks, the most common sources for olefinic feedstocks are light cracked hydrocarbon streams from an FCC unit, or a $C_4$ stream from a steam cracker after butadiene extraction or after selective hydrogenation of the butadiene to n-olefins.

Often the olefinic hydrocarbon feedstock will contain diolefins in addition to the desired monoolefin feed components. These diolefins deactivate the catalyst in downstream processes by polymerizing and forming heavy hydrocarbons that block the active sites of the catalyst and prevent their use. In a preferred embodiment, the hydrocarbon feed stream of the present invention can undergo treatment for the elimination of diolefins. A common method of eliminating diolefins is passing the hydrocarbon feed stream to a selective hydrogenation zone to saturate the diolefins into monoolefins. Suitable catalysts and operating conditions for such a selective dehydrogenation process can be found in U.S. Pat. Nos. 4,695,560 and 4,734,540, the contents of which are hereby incorporated by reference.

The selective hydrogenation process typically employs a nickel on alumina catalyst or a noble metal, such as palladium on alumina, for selective hydrogenation. The nickel may be sulfided or unsulfided. The process can also operate in a broad range of operating conditions including pressures of from about 40–800 psig, with pressures of between 50–300 psig being preferred, and temperatures of from about 70°–700° F., with temperatures of from about 120°–400° F. being preferred. Effective space velocities for the processes should be above 1 $hr^{-1}$ and preferably above 5 with a range of from about 5 to 35 $hrs^{-1}$. It is typical in such a process to limit the amount of hydrogen to prevent the saturation of monoolefins such that there is less than twice the stoichiometric amount of hydrogen required for the selective hydrogenation in the process. Preferably, the mole ratio of hydrogen to diolefinic hydrocarbons in the material will be in the range of from 1:1 to 1.8:1 and, in some cases, the hydrogen will be less than the stoichiometrically required amount of hydrogen.

The olefinic hydrocarbon feedstock of the present invention may also contain a variety of sulfur compounds. Generally, the feed stream contains about 1 to 5000 ppm by weight sulfur, and more typically from about 1–1000 ppm sulfur, calculated as elemental sulfur of the feedstock.

In one embodiment of the present invention, the olefinic hydrocarbon feedstock of the present invention is passed into a Mercaptan Extraction Unit. In a preferred embodiment, the olefinic hydrocarbon feedstock of the present invention can be passed to a mercaptan treating zone. In the mercaptan treating zone, the $H_2S$- and COS-depleted hydrocarbon feedstock is contacted with an alkaline scrubbing solution under mercaptan absorption conditions effective to produce a mercaptan-depleted stream and a mercaptide-containing scrubbing solution. The alkaline scrubbing solution may be selected from the group consisting of aqueous sodium hydroxide or aqueous ammonium hydroxide. The mercaptide-containing scrubbing solution is contacted with air or oxygen in the presence of an oxidation catalyst effective to regenerate the mercaptide-containing scrubbing solution. The temperature of the scrubbing solution ranges between about 10° and about 80° C., preferably about 20° C. and a pressure generally in the range of about 100 kPa absolute to about 3450 kPa absolute in order to keep the $H_2S$- and COS-depleted stream in the liquid phase. Additional information on the preferred mercaptan treating zone of the present invention can be found in U.S. Pat. Nos. 4,908,122 and 4,913,802 which are hereby incorporated by reference.

The olefinic hydrocarbon feedstock of the present invention may also contain nitrogen compounds including ammonia, light amines, dimethylformamide, N-methyl-pyrolydone, and nitriles having 1 to 3 carbon atoms, e.g., acetonitrile (ACN) and propionitrile. These nitrogen compounds can be removed from the hydrocarbon feed stream by passing the hydrocarbon feedstock of the present invention through a nitrogen removal zone, water wash zone, or a zone that performs hydrolysis to ammonia.

In accordance with the present invention, at least a portion of a hydrocarbon process stream of present invention is contacted with an isomerization catalyst in an alkane isomerization zone under conditions sufficient to selectively convert the normal alkane to isoalkane to produce an alkane isomerization zone effluent stream. Hydrocarbon process streams that are suitable as feed to the alkane isomerization zone include the olefinic hydrocarbon feedstock, the first separation zone effluent stream and the effluent from the alkene isomerization zone.

With respect to the alkane isomerization catalyst, a wide range of materials are known to be effective as a suitable catalyst including, but not limited to, such Lewis acids as $AlCl_3$, $GaCl_3$, $ZrCl_3$ and $Zr(SO_4)_2$.

With respect to the alkane isomerization conditions, the conditions are to be sufficient to selectively convert a normal alkane to an isoalkane. A wide range of operating conditions are employed in processes for selectively converting a normal alkane to an isoalkane. Many of these include vapor, liquid or mixed phase operations. In a preferred embodiment, liquid phase conditions are used.

The range of isomerization conditions to be used includes a temperature of 100°–350° F. with a pressure appropriate to ensure some liquid phase in the alkane isomerization zone.

In one embodiment of the present invention, at least a portion of the alkane isomerization zone effluent stream is passed to a first separation zone to produce a first separation zone and to remove the isoalkane component. The first separation zone may be any means known to those skilled in the art for separating a hydrocarbon process stream into its various fractions. In a preferred embodiment, the arrangement of the first separation zone consists of at least one distillation zone. In this distillation zone, a low boiling fraction comprising isoalkane can be removed from the overhead stream of the distillation zone. A high boiling fraction that principally comprises the combined etherification feed stream can be removed from the bottoms portion of the distillation zone.

A useful arrangement for the first separation zone of this invention is the use of a reactive distillation zone that contains a bed of alkane isomerization catalyst. Accordingly, the reactive distillation zone can be used as a combined reactor. The operating conditions employed in the reactive distillation zone are generally the same as those outlined herein for the alkane isomerization reaction zone. No particular apparatus or arrangement is needed to retain the catalyst bed within the distillation section of the reactive distillation zone and a variety of methods can be used to incorporate the bed or region of catalyst within the reactive distillation zone. For example, catalyst may be retained between suitable packing materials or may be incorporated onto a distillation tray itself. A preferred method of retaining the catalyst is through the use of a corrugated structural device that is described in U.S. Pat. No. 5,073,236 which is hereby incorporated by reference.

In one embodiment of the present invention, at least a portion of the olefinic hydrocarbon stream is contacted with an etherification catalyst in an etherification zone at etherification conditions to react isoalkene with an alcohol to produce an etherification zone effluent stream comprising the ether and normal alkane.

With respect to the etherification catalyst, a wide range of materials are known to be effective as etherification catalysts for the isoalkene reactants including mineral acids such as sulfuric acid, boron trifluoride, phosphoric acid on kieselguhr, phosphorous-modified zeolites, heteropoly acids and various sulfonated resins. The use of a sulfonated solid resin catalyst is preferred. These resin-type catalysts include the reaction products of phenolformaldehyde resins and sulfuric acid and sulfonated polystyrene resins including those cross-linked with divinylbenzene. A particularly preferred etherification catalyst is a macroporous acid form of a sulfonic ion exchange resin such as a sulfonated styrene-divinylbenzene resin as described in U.S. Pat. No. 2,922,822 having a degree of crosslinking of about 5 to 60%. Suitable resins are available commercially. Specialized resins have been described in the art and include copolymers of sulfonyl fluorovinyl ether and fluorocarbons as described in U.S. Pat. No. 3,489,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least about 400 $m^2$/g, a pore volume of about 0.6–2.5 ml/g and a mean pore diameter of 40–1000 Angstroms. It is contemplated that the subject process could be performed using a metal-containing resin which contains one or more metals from subgroups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929.

With respect to the etherification conditions, the conditions are to be sufficient to produce an etherification zone effluent stream comprising the tertiary alkyl ether and normal alkene. A wide range of operating conditions are employed in processes for producing tertiary alkyl ethers from isoalkene and alcohols. Many of these include vapor, liquid, or mixed-phase operations. Processes operating with vapor or mixed-phase conditions may be suitably employed in this invention. In a preferred embodiment, liquid phase conditions are used.

The range of etherification conditions for processes operating in liquid phase still includes a broad range of suitable conditions including a superatmospheric pressure sufficient to maintain the reactants as liquid phase, generally below about 700 psig, and a temperature between about 85° F. and about 210° F. Even in the presence of additional light materials, pressures in the range of about 140 to 580 psig are sufficient. A preferred temperature range is about 100°–210° F. The reaction rate is normally faster at higher temperatures, but conversion is more complete at lower temperatures due to favorable thermodynamics equilibrium. High conversion in a moderate volume reaction zone can, therefore, be obtained if the initial section of the reaction zone, e.g., the first two thirds, is maintained above 160° F. and the remainder of the reaction zone is maintained below 120° F. This may be accomplished most easily with two reactors. The ratio of alcohol to isoalkene should normally be maintained in the range of about 1:1 to 2:1, preferably 1.1:1 to 1.5:1. An excess of alcohol, above that required to achieve satisfactory conversion at good selectivity, should be avoided as some decomposition of the alcohol may occur. A description of suitable etherification processes useful for the present invention can be found in U.S. Pat. Nos. 4,219,678 to Obenaus et al. and 4,282,389 to Droste et al. which are incorporated herein.

The etherification zone operates selectively to principally convert only isoalkenes. Therefore, alkanes and normal alkenes pass through the etherification zone without any significant conversion to products or by-products. Thus, the etherification zone effluent together with the unreacted feed components provide a stream of ether product and normal and branched alkenes and alkane isomers for separation.

The alcohols that can be used in the etherification zone are typically $C_1$–$C_5$ monohydroxy alcohols. Methanol typically constitutes the alcohol of choice for the etherification process. Ethanol, although used less often, is also a commonly-available alcohol for the etherification process.

In one embodiment of the present invention, at least a portion of the etherification zone effluent stream is passed to a second separation zone to separate the etherification product from the unreacted reactants. The second separation zone produces an ether product stream and an overhead raffinate stream comprising a normal alkene. The second separation zone can be any means known to those skilled in the art for separating a hydrocarbon process stream into its various fractions. In a preferred embodiment, the arrangement of the second separation zone consists of at least one distillation zone. In this distillation zone, a low boiling fraction comprising isoalkane and alcohol can be removed from the overhead stream of the distillation zone. In addition, the overhead stream can contain a normal alkene that was not reacted in the etherification zone and a normal alkane that entered the etherification zone as part of the hydrocarbon feed stream of the present invention. A high boiling fraction that principally comprises the ether product can be removed from the bottoms portion of the distillation zone.

A useful arrangement for the second separation zone is the use of a reactive distillation zone that contains a bed of etherification catalyst. The distillation zone can provide additional etherification of the unreacted isoalkene. Accordingly, the reactive distillation zone can be used as a combined reactor. Processes for the production of ethers by reactive distillation are taught in U.S. Pat. Nos. 3,634,535 and 4,950,803. The operating conditions employed in the reactive distillation zone are generally the same as those outlined herein for the etherification reaction zone. No particular apparatus or arrangement is needed to retain the catalyst bed within the distillation section of the reactive distillation zone and a variety of methods can be used to incorporate the bed or region of catalyst within the reactive distillation zone. For example, catalyst may be retained between suitable packing materials or may be incorporated onto a distillation tray itself. A preferred method of retaining the catalyst is through the use of a corrugated structural device that is described in U.S. Pat. No. 5,073,236 which is hereby incorporated by reference.

In a preferred embodiment, the second separation zone effluent stream is passed to an alcohol recovery zone. The alcohol recovery zone generally consists of a water wash zone and an alcohol-water fractionation zone. In the water wash zone, a water-containing stream enters the top of the zone and countercurrently contacts the second separation zone effluent stream to remove the alcohol. Suitable operating conditions for the water wash zone include a temperature of about 100° F., a pressure of about 100 psi, and a water to alcohol ratio of about 6 to 1.

In one embodiment of the present invention, at least a portion of the second separation zone effluent stream is passed to an alkene isomerization zone containing an isomerization catalyst at isomerization conditions sufficient to produce an isoalkene-containing isomerate.

Methods for converting the normal alkene components to isoalkene by isomerization are well known in the art. Catalysts and methods for the skeletal isomerization of linear alkenes are described in U.S. Pat. Nos. 4,778,943 and 4,814,519. A preferred catalyst for the isomerization reaction zone of the present invention is a non-zeolitic molecular sieve. Preferred forms of the non-zeolitic molecular sieve include silicoaluminophosphates and a magnesium aluminophosphate. Suitable non-zeolitic catalysts such as the SAPO and MgAPO are described in U.S. Pat. Nos. 4,440,871 and 4,758,419 which are hereby incorporated by reference. The catalyst for the isomerization zone typically lies in a fixed bed arrangement. In order to permit in situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01:1 to 9:1, and preferably in a ratio of from about 1:1 to 7:1, aids the process by suppressing the formation of carbon compounds on the catalyst.

The alkene isomerization zone is typically operated over a broad range of conditions including temperatures of from about 100° to 1300° F. with temperatures in the range of about 200° to 1000° F. being preferred. Pressures for the isomerization reaction can vary over a wide range extending from atmospheric conditions to 700 psig, preferably 25 to 350 psig. Space velocities can also vary over a wide range from 0.5 to 100 $hr^{-1}$ with a preferred range of 1 to 15 $hr^{-1}$. The per pass conversion of normal alkenes to isoalkenes in the isomerization zone will typically exceed 35% of the total combined feed for $C_4$ hydrocarbons and 50% of the total combined feed for $C_5$ hydrocarbons.

In a preferred embodiment, the effluent stream from the isomerization zone is passed to a stripping zone for removal of light ends, such as methane and hydrogen. The hydrogen can be recovered and recycled to the inlet of the isomerization zone to provide any necessary hydrogen concentration. It may also be desirable to remove the heavier ends from the isoalkene-containing isomerate.

In one embodiment of the present invention, the isoalkene-containing isomerate is first passed to the alkane isomerization zone for conversion of normal alkanes and then passed to a separation zone for removal of isoalkanes. Under this embodiment, the resulting effluent from the alkane isomerization zone is passed to the etherification zone.

In another embodiment, i.e., the embodiment where the olefinic hydrocarbon feedstock is passed to the alkane isomerization zone, the isoalkane-containing isomerate is passed directly to the etherification zone.

Referring to the figure, a $C_4$ hydrocarbon feed stream from a fluidized catalytic cracking unit (not shown) enters etherification feed pretreatment zone 4 via line 2. In etherification feed pretreatment zone 4, the $C_4$ olefinic hydrocarbon feed stream is treated to remove contaminants that can adversely affect the etherification catalyst. Accordingly, etherification feed pretreatment zone 4 consists of a nitrogen removal unit, a selective hydrogenation unit, and a sulfur treatment unit (all not shown) as required, i.e., not necessarily all at once. A purified $C_4$ olefinic hydrocarbon feed stream exits etherification pretreatment zone 4 through line 6. The treated $C_4$ olefinic hydrocarbon feed stream is then admixed with an isobutene-containing isomerate shown as line 34 from butene isomerization zone 26 to form an etherification feed stream.

The resulting etherification feed stream enters butane isomerization zone 8 via line 7. Butane isomerization zone 8 is a reactive distillation zone that contains a bed 9 of butane isomerization catalyst for selectively converting normal butane to isobutane and for simultaneously separating the isobutane from the etherification feed stream by fractionation. Operating conditions for butane isomerization zone 8 are a temperature of about 100°–450° F. and a pressure sufficient to maintain a liquid phase in butane isomerization zone 8. The isobutane exits butane isomerization zone 8 through line 10. The resulting etherification feed stream exits butane isomerization zone 8 by line 12 and is admixed with methanol from line 14 to form a combined etherification feed stream.

The combined etherification feed stream is fed to etherification zone 16 via line 15. In etherification zone 16, isobutene is reacted with methanol in the presence of an etherification catalyst comprising a macroporous acid-form sulfonated solid resin at a temperature of about 170° F. and a pressure of about 88 psi to form methyl tertiary butyl ether (MTBE). Catalyst in etherification zone 16 is disposed in a fixed bed reactive distillation column arrangement. Etherification zone 16 also contains a separation zone comprising a reactive distillation unit (not shown) for separating the etherification effluent into an MTBE product stream and a raffinate. The MTBE product stream exits etherification zone 16 through line 17. The raffinate stream comprising methanol and normal butene exits etherification zone 16 at line 18.

The raffinate stream enters methanol recovery zone 20 via line 18 for removal of methanol. Methanol recovery zone 20 includes a water wash column for extracting the methanol and a fractionation column for separating the methanol from the water (both not shown). Recovered methanol is recycled to etherification zone 16 through line 22.

After methanol recovery, the raffinate stream is passed to butene isomerization zone 26 via line 24. In isomerization zone 26, skeletal isomerization of normal butene to isobutene occurs in the presence of a silicoaluminophosphate catalyst of the SAPO-11 type at a temperature of about 200°–1000° F. and a pressure of about 25–350 psi.

Effluent from butene isomerization zone 26 exits at line 28 and is passed to stripper zone 30 to remove any light ends via line 32. The resulting effluent is then admixed with the etherification feed stream through line 34.

EXAMPLES

Introduction

The upcoming examples are based on a process scheme that includes introducing an etherification feed into a reactive-distillation etherification zone to produce an overhead raffinate comprising normal butanes and butenes and a bottoms stream comprising MTBE (in barrels per day). In this etherification/isomerization loop, the raffinate stream is passed to a feed splitter which fractionates out light ends from the raffinate prior to feeding the raffinate to a butene isomerization unit. The effluent from the butene isomerization unit is sent to a stripper to remove light ends and then mixed with fresh feed and introduced to the etherification unit.

Figure 2:
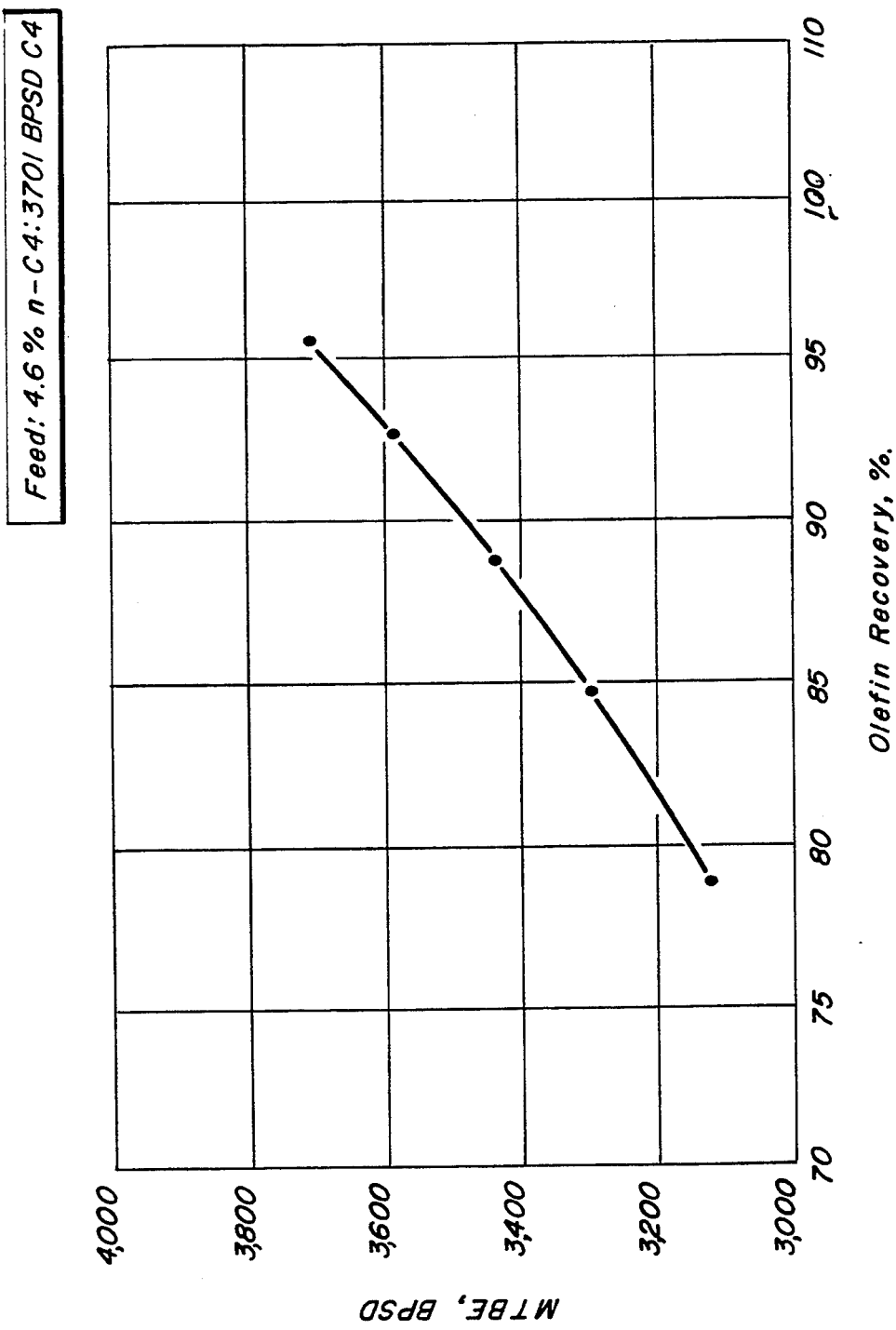
FIG. 2 is a plot of % olefin recovery across the reactive-distillation etherification tower versus the amount of methyl tertiary butyl ether produced.

FIG. 2 illustrates the effect of olefin recovery across the reactive-distillation zone on the total MTBE production. This figure shows that olefin recovery in the reactive-distillation etherification zone can have a significant impact on MTBE production. For example, at an olefin recovery of 80% the MTBE production is about 3150 barrels per day, whereas an olefin recovery of 95% can significantly increase the production of MTBE to about 3700 barrels per day. Clearly maintaining high olefin recovery is desirable.

EXAMPLE 1

Olefin recovery suffers when fractionation is used as the means of minimizing the buildup of normal butanes in the etherification/isomerization loop because olefins are lost with the normal butanes. The present invention solves this problem by converting the normal butanes to isobutanes (a lighter component) which can be more readily removed by distillation.

The concentration of normal butane in the etherification/isomerization loop can have a significant effect on both the olefin recovery and the amount of combined feed sent to the butene isomerization reactor.

Figure 3:
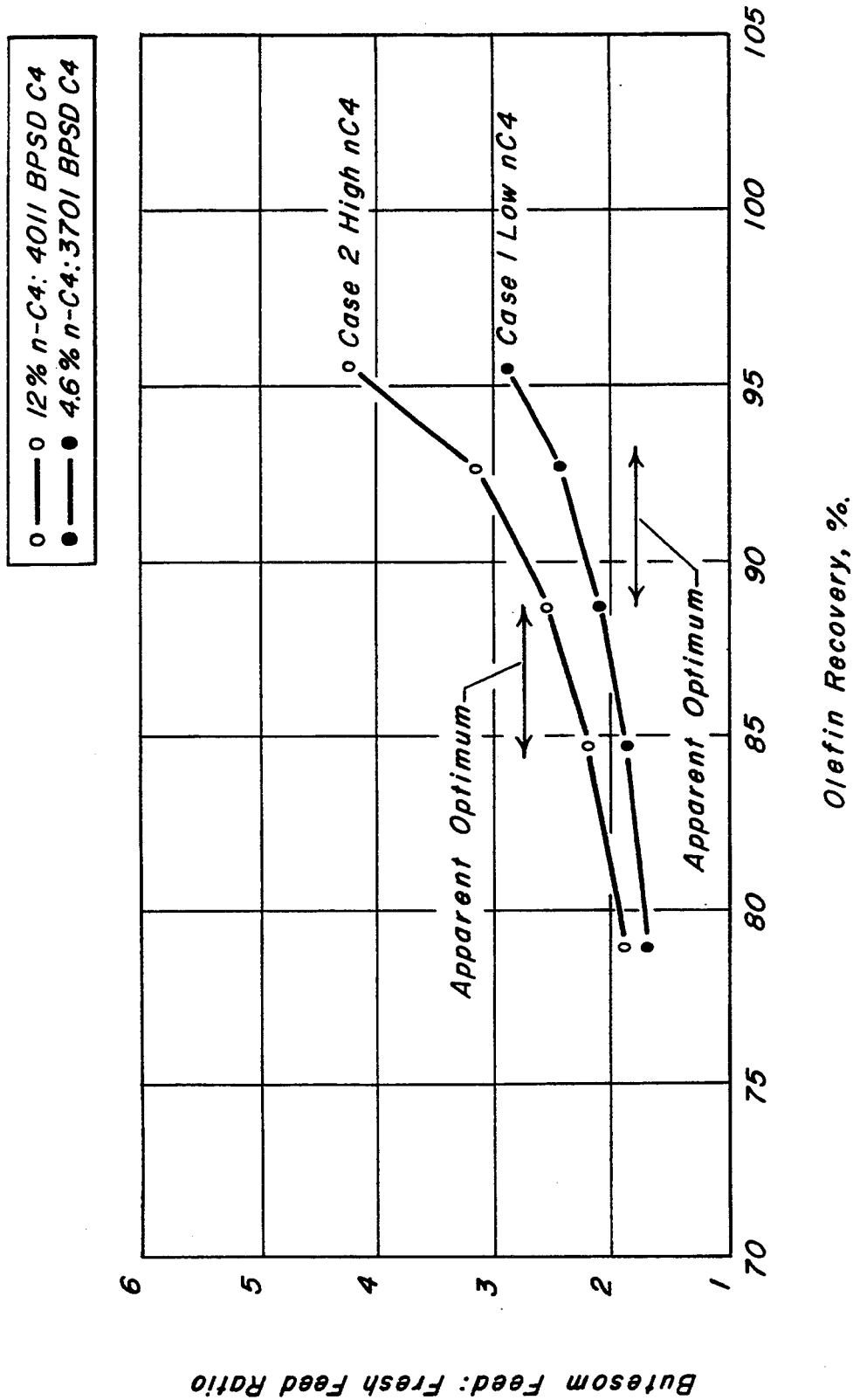
FIG. 3 is a plot of % olefin recovery across the reactive-distillation etherification tower versus the fresh feed ratio to the butene isomerization unit.

FIG. 3 is a plot of % olefin recovery in the overhead stream of the reaction with distillation tower (etherification) versus the combined feed ratio going to the butene isomerization zone. FIG. 3 illustrates two cases. Case 1 is the low normal butane case having the feed composition shown below in Table 1.

TABLE 1

| Feed Composition, BSPD | Case 1 |
|---|---|
| $H_2$ | 1.8 |

TABLE 1-continued

| Feed Composition, BSPD | Case 1 |
|---|---|
| $CH_4$ | 11.3 |
| $C_3$ | 4.3 |
| $i\text{-}C_4=$ | 893.5 |
| $1\text{-}C_4=$ | 1620.2 |
| cis-2, $C_4=$ | 385.1 |
| trans-2, $C_4=$ | 592.8 |
| $i\text{-}C_4$ | 20.4 |
| $n\text{-}C_4$ | 171.2 |
| TOTAL | 3701.0 |

Case 2 is the high normal butane case where the combined feed had a composition shown below in Table 2.

TABLE 2

| Feed Composition, BSPD | Case 2 |
|---|---|
| $H_2$ | 1.8 |
| $CH_4$ | 11.3 |
| $C_3$ | 4.3 |
| $i\text{-}C_4=$ | 893.5 |
| $1\text{-}C_4=$ | 1620.2 |
| cis-2, $C_4=$ | 385.1 |
| trans-2, $C_4=$ | 592.8 |
| $i\text{-}C_4$ | 20.4 |
| $n\text{-}C_4$ | 481.3 |
| TOTAL | 4011.0 |

In both cases, it is shown that increases in olefin recovery can be achieved but only at the expense of increases in the amount of combined feed to the butene isomerization zone. However, in Case 2 that increase is considerably higher at higher olefin recoveries. For example, in order to achieve 90% olefin recovery the combined feed ratio to the butene isomerization unit has to be only about 2.8, but to increase the olefin recovery to 95% the combined feed ratio jumps to about 4.1. In contrast, in Case 1 in order to achieve 90% olefin recovery the combined feed to the butene isomerization unit has to be about 2.2, and to increase the olefin recovery to 95% the combined feed ratio increases to only 2.9. Clearly, the low normal butane case is more economically attractive due to the lower combined feed rate translating into lower capital cost for the etherification/isomerization method. It should also be pointed out that the differences in combined feed rates between Cases 1 and 2 increase dramatically at higher rates at higher olefin recoveries.

Figure 4:
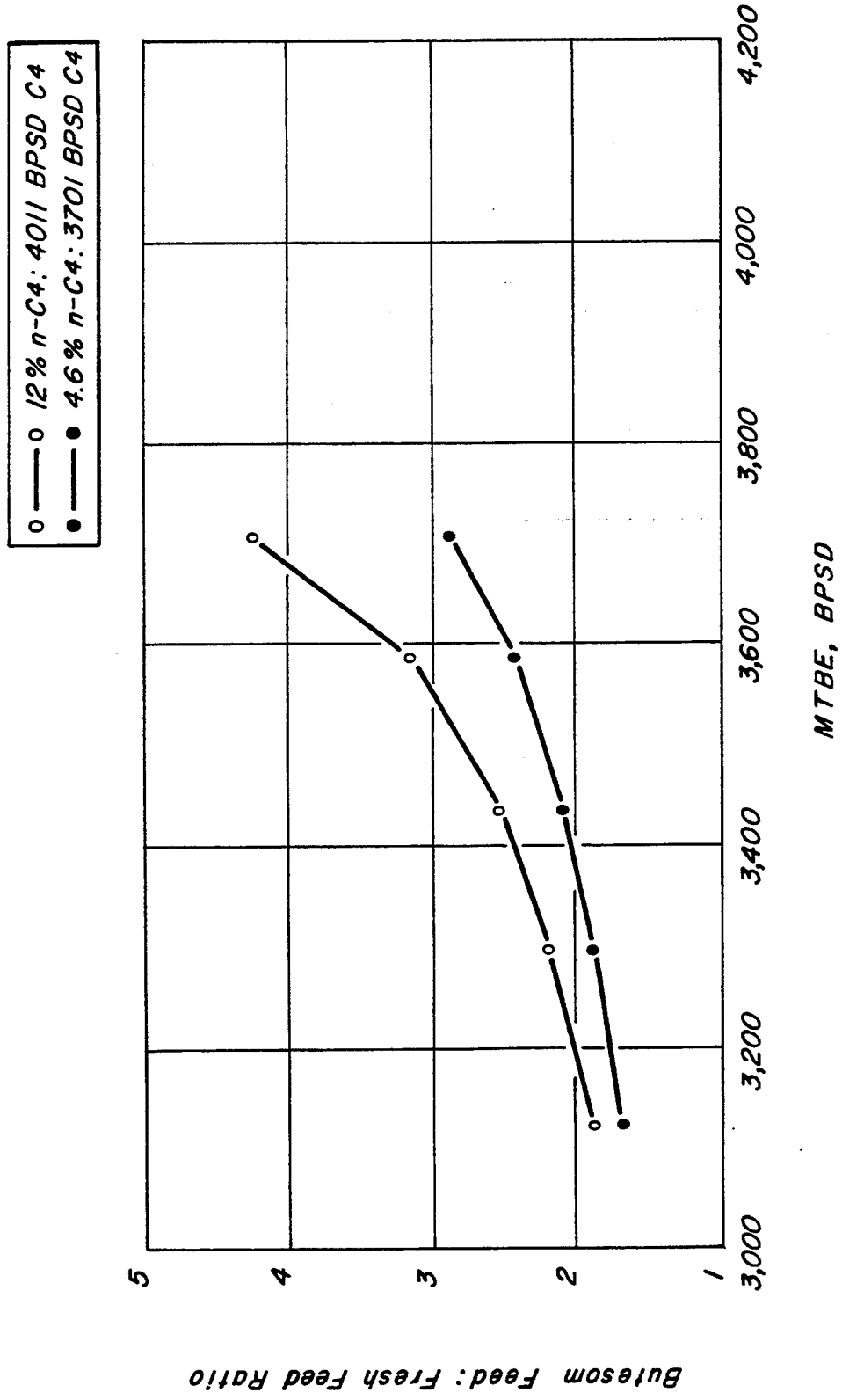
FIG. 4 is a plot of barrels per day of MTBE produced versus the fresh feed ratio to the butene isomerization unit.

FIG. 4 is a plot of barrels per day of MTBE produced versus combined feed to the butene isomerization unit. The upper curve in FIG. 4 represents the high normal butane case (12% normal butane per 4011 barrels per day). The bottom curve represents the low normal butane case (4.6% normal butane per 3701 barrels per day). FIG. 4 shows that to increase the MTBE production one must increase the combined feed.

EXAMPLE 2

The following analysis was done to provide technical support for the present invention. The analysis was based on computer simulation.

The process scheme tested was the one described above in the Introduction section. The feed to the reactive-distillation etherification reactor was 4.7% normal butane, 0% isobutane, and 96.3% isobutylene. The units used are shown below in Table 3 along with the rules for normal butane and isobutane splits:

TABLE 3

|  | n-$C_4$ loss | i-$C_4$ loss |
|---|---|---|
|  | % of feed to specific unit | |
| (1) Etherification zone | 0% | 0% |
| (2) Splitter | 4.2% | 15.2% |
| (3) Butene Isomerization | ← net production → | |
| (4) Post-Butene Isomerization | Consumption | Production |
| (5) Stripper | 0.7% | 3.1% |

The equilibrium of normal butane to isobutane was 69% at 150° C.

The results are shown below in Table 4.

TABLE 4

| n-$C_4$ conversion | 0% | 5% | 10% | 20% | 40% | 60% |
|---|---|---|---|---|---|---|
| n-$C_4$ (But feed) | 0.958 | 0.481 | 0.320 | 0.189 | 0.102 | 0.068 |
| i-$C_4$ (But feed) | 0.035 | 0.148 | 0.186 | 0.217 | 0.237 | 0.245 |
| Total (But feed) | 0.999 | 0.629 | 0.506 | 0.406 | 0.339 | 0.314 |

The above calculations indicate that normal butane isomerization to isobutane can be used to prevent the buildup of paraffins in the olefin isomerization loop. Although not wanting to be limited by theory, it is believed that this happened because the boiling point of isobutane is less than the boiling point of normal butane and therefore isobutane can be removed more effectively using a fractionation column to take the isobutane overhead. It is interesting to know that merely 5% conversion of normal butane to isobutane can result in a 37% reduction of the butanes in the feed to the olefin isomerization unit.

What is claimed:

1. A process for the production of a tertiary alkyl ether from an olefinic hydrocarbon feedstock comprising normal alkane, isoalkenes and isoalkane which process comprises the steps of:
   (a) contacting at least portion of said feedstock with an isomerization catalyst in an alkane isomerization zone under conditions sufficient to selectively convert said normal alkane to isoalkane to produce an alkane isomerization zone effluent stream;
   (b) passing at least a portion of said alkane isomerization zone effluent stream to a first separation zone to produce a first separation zone effluent stream and to remove isoalkane;
   (c) contacting at least a portion of said first separation zone effluent stream with an etherification catalyst in an etherification zone at etherification conditions sufficient to react said isoalkene with a $C_1$-$C_5$ monohydroxy alcohol to produce an etherification zone effluent stream comprising said ether and normal alkane;
   (d) passing at least a portion of said etherification zone effluent stream to a second separation zone to produce an ether product stream and an overhead raffinate stream comprising normal alkene;
   (e) contacting at least a portion of said overhead raffinate stream with an isomerization catalyst in an alkene isomerization zone at isomerization conditions sufficient to convert said normal alkene to isobutene, thereby producing an isoalkene-containing isomerate; and
   (f) recycling at least a portion of said isoalkene-containing isomerate to said alkane isomerization zone.

2. The process of claim 1 wherein said first separation zone comprises a reactive distillation zone containing a bed of isomerization catalyst.

3. The process of claim 1 wherein said second separation zone comprises a reactive distillation zone containing a bed of etherification catalyst.

4. The process of claim 1 wherein said etherification catalyst comprises a macroporous acid-form sulfonated solid resin.

5. The process of claim 1 further comprising passing said isoalkene-containing isomerate into a stripper zone to remove light ends.

6. The process of claim 1 wherein said alcohol comprises methanol and/or ethanol.

7. The process of claim 1 wherein said alkane is butane.

8. The process of claim 1 wherein said second separation zone effluent stream is passed into an alcohol recovery zone.

9. A process for the production of methyl tertiary butyl ether from an olefinic hydrocarbon feedstock comprising normal butane, isobutene, normal butene and isobutane which process comprises the steps of:
   (a) contacting at least portion of said feedstock with an isomerization catalyst in a butane isomerization zone under conditions sufficient to selectively convert said normal butane to isobutane to produce a butane isomerization zone effluent stream;
   (b) passing at least a portion of said butane isomerization zone effluent stream to a first separation zone to produce a first separation zone effluent stream and to remove isobutane;
   (c) contacting at least a portion of said first separation zone effluent stream with an etherification catalyst comprising a macroporous add-form sulfonated solid resin in an etherification zone at etherification conditions sufficient to react said isobutene with a methanol to produce an etherification zone effluent stream comprising said methyl tertiary butyl ether and said normal butene;
   (d) passing at least a portion of said etherification zone effluent stream to a second separation zone to produce a methyl tertiary butyl ether product stream and a second separation zone effluent stream comprising normal butene;
   (e) contacting at least a portion of said second separation zone effluent stream in the presence of an isomerization catalyst in a butene isomerization zone at isomerization conditions sufficient to convert said normal butene to isobutene, thereby producing an isobutene-containing isomerate; and
   (f) recycling at least a portion of said isobutene-containing isomerate to said butane isomerization zone.

10. The process of claim 9 wherein said first separation zone comprises a reactive distillation zone containing a bed of butane isomerization catalyst.

11. The process of claim 9 further comprising passing said isobutene-containing isomerate to a stripper zone to remove light ends.

12. The process of claim 9 wherein said second separation zone effluent stream is passed to an alcohol recovery zone.

13. A process for the production of methyl tertiary butyl ether from an olefinic hydrocarbon feedstock comprising normal butane, normal butene, isobutene and isobutane which process comprises the steps of:
   (a) passing said olefinic feedstock into a selective hydrogenation zone for converting any diolefins present to monoolefins;
   (b) contacting at least a portion of the feedstock resulting from step (a) with an isomerization catalyst in a butane isomerization zone under conditions sufficient to selectively convert said normal butane to isobutane to produce a butane isomerization zone effluent stream;

(c) passing at least a portion of said butane isomerization zone effluent stream to a first reactive-distillation zone to remove isobutane;

(d) contacting at least a portion of the resulting butane isomerization zone effluent stream with an etherification catalyst comprising a macroporous acid-form sulfonated solid resin in an etherification zone at etherification conditions sufficient to react said isobutene with a methanol to produce an etherification zone effluent stream comprising said methyl tertiary butyl ether and said normal butene;

(e) passing at least a portion of said etherification zone effluent stream to a second reactive-distillation zone to produce a methyl tertiary butyl ether product stream and a second reactive-distillation zone effluent stream comprising normal butene;

(f) passing said second reactive distillation zone effluent stream to a water wash tower wherein said second reactive distillation zone effluent stream is contacted with water to produce a raffinate stream comprising normal butene and an extract stream comprising water and methanol;

(g) contacting at least a portion of said raffinate stream with an isomerization catalyst in a butene isomerization zone at isomerization conditions sufficient to convert said normal butene to isobutene, thereby producing an isobutene-containing isomerate; and (h) recycling at least a portion of said isobutene-containing isomerate to said butane isomerization zone.

14. A process for the production of a tertiary alkyl ether from an olefinic hydrocarbon feedstock comprising normal alkane, isoalkene, normal alkene and isoalkane which process comprises the steps of:

(a) contacting at least a portion of said olefinic hydrocarbon feedstock with an etherification catalyst in an etherification zone at etherification conditions sufficient to react said isoalkene with a $C_1$–$C_5$ monohydroxy alcohol to produce an etherification zone effluent stream comprising said ether and normal alkane;

(b) passing at least a portion of said etherification zone effluent stream to a first separation zone to produce an ether product stream and a first separation zone effluent stream comprising normal alkene;

(c) contacting at least a portion of said first separation zone effluent stream with an isomerization catalyst in an alkene isomerization zone at isomerization conditions sufficient to convert said normal alkene to isobutene, thereby producing an alkene isomerization zone effluent stream comprising isoalkene and normal alkane; and (d) contacting at least portion of said alkene isomerization zone effluent stream with an isomerization catalyst in an alkane isomerization zone under conditions sufficient to selectively convert said normal alkane to isoalkane to produce an alkane isomerization zone effluent stream; and (e) passing said alkane isomerization zone effluent to a second separation zone to produce a second separation zone effluent stream and to remove isoalkanes;

(f) recycling at least a portion of said second separation zone effluent stream to said etherification zone.

15. The process of claim 14 wherein said first separation zone comprises a reactive distillation zone containing a bed of isomerization catalyst.

16. The process of claim 14 wherein said second separation zone comprises a reactive distillation zone containing a bed of etherification catalyst.

17. The process of claim 14 wherein said etherification catalyst comprises a macroporous acid-form sulfonated solid resin.

18. The process of claim 14 further comprising passing said alkene isomerization zone effluent stream to a stripper zone to remove light ends.

19. The process of claim 14 wherein said alcohol comprises methanol and/or ethanol.

20. The process of claim 14 wherein said alkane is butane.

21. The process of claim 14 wherein said first separation zone effluent stream is passed into an alcohol recovery zone.

22. A process for the production of methyl tertiary butyl ether from an olefinic hydrocarbon feedstock comprising diolefins, normal butane, normal butene, isobutene and isobutane which process comprises the steps of:

(a) passing said olefinic hydrocarbon feedstock into a selective hydrogenation zone for converting said diolefins to monoolefins;

(b) contacting at least a portion of the resulting olefinic hydrocarbon stream with an etherification catalyst comprising a macroporous acid-form sulfonated solid resin in an etherification zone at etherification conditions sufficient to react said isobutene with a methanol to produce an etherification zone effluent stream comprising said methyl tertiary butyl ether, normal butane and normal butene;

(c) passing at least a portion of said etherification zone effluent stream to a first reactive-distillation zone to produce a methyl tertiary butyl ether product stream and a first reactive-distillation zone effluent stream comprising normal butene and normal butane;

(d) passing said first reactive-distillation zone effluent stream to a methanol wash zone to produce a raffinate comprising normal butane and normal butene and an extract comprising methanol and water;

(e) contacting at least a portion of said raffinate stream with an isomerization catalyst in a butene isomerization zone at isomerization conditions sufficient to convert said normal butene to isobutene, thereby producing a butene isomerization zone effluent stream comprising isobutene and normal butane;

(f) contacting at least a portion of said butene isomerization zone effluent stream with an isomerization catalyst in a butane isomerization zone under conditions sufficient to selectively convert said normal butane to isobutane to produce a butane isomerization zone effluent stream comprising isobutene and isobutane;

(g) passing at least a portion of said butane isomerization zone effluent stream to a second reactive-distillation zone to produce a second reactive-distillation zone effluent stream comprising isobutene and to remove isobutane; and (h) recycling at least a portion of said second reactive-distillation zone effluent stream to said etherification zone.

* * * * *